(12) United States Patent
Shepard et al.

(10) Patent No.: US 12,721,601 B2
(45) Date of Patent: Sep. 1, 2026

(54) ULTRASOUND PHASED ARRAY ON FLEXIBLE CMOS AND METHODS FOR FABRICATING HEREOF

(71) Applicant: The Trustees of Columbia University in the City of New York, New York, NY (US)

(72) Inventors: Kenneth L. Shepard, Ossining, NY (US); Tiago Costa, New York, NY (US); Kevin Tien, New York, NY (US); Chen Shi, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 18/415,956

(22) Filed: Jan. 18, 2024

(65) Prior Publication Data

US 2024/0407757 A1 Dec. 12, 2024

Related U.S. Application Data

(62) Division of application No. 16/474,986, filed as application No. PCT/US2017/068528 on Dec. 27, 2017, now Pat. No. 11,937,981.

(60) Provisional application No. 62/439,680, filed on Dec. 28, 2016.

(51) Int. Cl.
*A61B 8/00* (2006.01)
*A61N 7/00* (2006.01)

(52) U.S. Cl.
CPC .......... *A61B 8/4488* (2013.01); *A61B 8/4494* (2013.01); *A61B 8/42* (2013.01); *A61N 2007/0026* (2013.01); *A61N 2007/0086* (2013.01)

(58) Field of Classification Search
CPC ....... A61B 8/4488; A61B 8/4494; A61B 8/42; A61N 2007/0026; A61N 2007/0086; A61N 2007/0095; A61N 7/00
See application file for complete search history.

(56) References Cited

U.S. PATENT DOCUMENTS 9,735,893 B1 * 8/2017 Aleksov ............... A61B 5/0024
9,766,328 B2 * 9/2017 Black .................. G01S 15/8902
10,118,054 B2 * 11/2018 Maharbiz ............. A61B 6/4258
11,071,519 B2 * 7/2021 Nowak ................ A61B 8/5223
2007/0088297 A1 * 4/2007 Redding ........... A61M 37/0092
604/289
2008/0027320 A1 * 1/2008 Bolorforosh .......... B06B 1/0629
600/439

(Continued)

OTHER PUBLICATIONS

International Search Report and Written Opinion for International Patent Application No. PCT/US2017/068528 mailed on Mar. 13, 2018.

*Primary Examiner* — Sanjay Cattungal
(74) *Attorney, Agent, or Firm* — Hunton Andrews Kurth LLP

(57) ABSTRACT

An ultrasound phased array integrated in flexible CMOS technology is provided. The CMOS IC chip is fabricated through various chip-thinning techniques, resulting in mechanical flexibility, robustness, and minimized mechanical loading for the piezoelectric transducers. The ultrasound phased array CMOS patch can allow for the generation of high intensity focal regions for maximum penetration in regions of interest.

8 Claims, 12 Drawing Sheets

(56) References Cited

U.S. PATENT DOCUMENTS

| | | | | |
|---|---|---|---|---|
| 2011/0009734 | A1 | 1/2011 | Foley et al. | |
| 2011/0123783 | A1* | 5/2011 | Sherrer | H01F 41/14 156/247 |
| 2011/0237953 | A1 | 9/2011 | Olsson et al. | |
| 2013/0043768 | A1 | 2/2013 | Cochran et al. | |
| 2014/0219062 | A1 | 8/2014 | Rothberg et al. | |
| 2014/0303452 | A1* | 10/2014 | Ghaffari | A61B 18/20 601/3 |
| 2014/0367786 | A1* | 12/2014 | Bedell | H10D 84/85 257/369 |
| 2015/0032002 | A1* | 1/2015 | Rothberg | A61B 8/4488 600/440 |
| 2015/0340346 | A1* | 11/2015 | Chu | H01L 25/0753 257/89 |
| 2016/0157717 | A1* | 6/2016 | Gaster | A61B 5/02416 600/301 |
| 2016/0303402 | A1 | 10/2016 | Tyler | |
| 2017/0350817 | A1* | 12/2017 | Sriram | G01N 33/22 |

* cited by examiner

300
Ni
Cr/Au
PR
PZT
PR
304
302
308
306

300
308
Ni
Cr/Au
PZT
Cr/Au
ICP Mask
Top Metalization
302
Bottom Metalization

300
Ni
Cr/Au
PZT
Cr/Au
ACF
SiO2
Signal
GND
ASIC
306
310
302
202

300
PZT
302

300
ACF
SiO2
Signal
GND
ASIC
310
202

ULTRASOUND PHASED ARRAY ON FLEXIBLE CMOS AND METHODS FOR FABRICATING HEREOF

CROSS REFERENCE TO RELATED APPLICATION(S)

This application is a divisional of U.S. patent application Ser. No. 16/474,986 filed on Jun. 28, 2019, and also relates to, and claims the benefits and priority from International Patent Application No. PCT/US2017/068528 filed Dec. 27, 2017 that published as International Patent Publication No. WO 2018/125912 on Jul. 5, 2018, which claims the benefit and priority from U.S. Provisional Patent Application No. 62/439,680 filed on Dec. 28, 2016, the entire disclosures of which are incorporated herein by reference.

STATEMENT REGARDING FEDERALLY SPONSORED RESEARCH

This invention was made with government support under grant HR0011-15-2-0054 awarded by DOD/DARPA. The government has certain rights in the invention.

BACKGROUND

With the development of certain neuromodulation and neural interfaces that provide a path for communication with the central and peripheral nervous systems, there is a need for providing high spatial resolution and depth while remaining portable and non-invasive in order to contain diverse effects to the patient.

Specifically, when spatial resolution and depth of penetration are sought, interface systems can be implanted in the peripheral and central nervous system (PNS/CNS) at the desired depth, which can involve expensive and risky surgery procedures involving implantable electrodes, such as in peripheral nerve blocking and deep brain stimulation, or optical based shanks for optogenetics. On the other hand, certain non-invasive techniques such as transcranial direct-current stimulation (tDCS) and transcranial magnetic stimulation (TMS) can achieve neuromodulation in the human cortex. However, such techniques can suffer from reduced spatial resolution and high attenuation with increasing depth, preventing their use for regions below the surface of the cortex.

Using ultrasound to achieve neuromodulation in the PNS and CNS (transcranial focused ultrasound (tFUS)) can provide for both good spatial resolution and depth of penetration while remaining non-invasive. Depth of penetration can be greater than with electromagnetic and optical interfaces due to the reduced wavelength of ultrasound waves, while spatial resolution can be controlled by focusing the ultrasound beam into the neural region of interest. In the CNS, by using frequencies below 1 MHz, tFUS can stimulate neurons anywhere in the brain with spatial resolution from 1 mm. In addition, ultrasound stimulation can avoid genetic modification of neurons which can result from optical stimulation. However, certain commercially available equipment based on traditional ultrasound imaging systems can be expensive, bulky and require specialized personnel for operation.

As a result, there is a need for ultrasound systems that can be highly miniaturized, conform to the body local curvature and achieve the necessary focal pressure, by tightly controlling the phase of the ultrasound wave of each ultrasound transducer, and scaling the number of transducers to achieve the required pressure.

SUMMARY

An ultrasound phased array patch on flexible Complimentary Semi-Oxide-Semiconductor (CMOS) and methods for fabricating thereof are disclosed herein.

In some embodiments, a non-invasive, wearable device for interfacing with the nervous system is disclosed having a flexible integrated circuit that includes a plurality of transmitting circuits and a plurality of receiving circuits configured to dynamically adapt one or more parameters for transmitting and receiving one or more ultrasound signals based on a selected mode of operation. In addition, the device also includes a plurality of ultrasound transducers coupled to the flexible integrated circuit and configured to generate the one or more ultrasound signals.

In some embodiments, the flexible wearable device is configured to operate in an imaging mode and/or a stimulation mode. In some embodiments, the device can alternate between the two operation modes. In addition, in some embodiments the flexible integrated circuit can further include a digital control unit for controlling one or more parameters for transmitting and receiving one or more ultrasound signals.

The disclosed subject matter also provides a system for non-invasive neural monitoring and stimulation including the non-invasive, wearable device that is configured to transmit and receive a plurality of ultrasound signals associated with a mode of operation, and a processor coupled to the non-invasive, wearable device that is configured to select the mode of operation.

The disclosed subject matter also provides a method for fabricating a non-invasive, wearable device for neural monitoring and stimulation including thinning a Complimentary Semi-Oxide-Semiconductor (CMOS) integrated circuit to a pre-determined thickness causing the CMOS integrated circuit to become flexible, integrating a plurality of ultrasound transducers onto the CMOS integrated circuit, wherein each of the ultrasound transducers includes a top side and a bottom side, and depositing a metal layer on the top side and bottom side of each of the plurality of ultrasound transducers to form electrodes that are electrically coupled to the CMOS integrated circuit.

In some embodiments, the fabrication method also includes depositing a photoresist layer on the top side and the bottom side of each of the plurality of ultrasound transducers. Further, in some embodiments, patterning is also performed on the plurality of ultrasound transducers that are integrated onto the CMOS integrated circuit. In some embodiments, the patterning includes using a dicing process to form a plurality of ultrasound transducer pillars.

The disclosed subject matter also provides filling the kerfs formed between the plurality of ultrasound transducer pillars with a biocompatible epoxy.

The accompanying drawings, which are incorporated and constitute part of this disclosure, illustrate embodiments of, and serve to explain the principles of, the disclosed subject matter.

Figure 1:
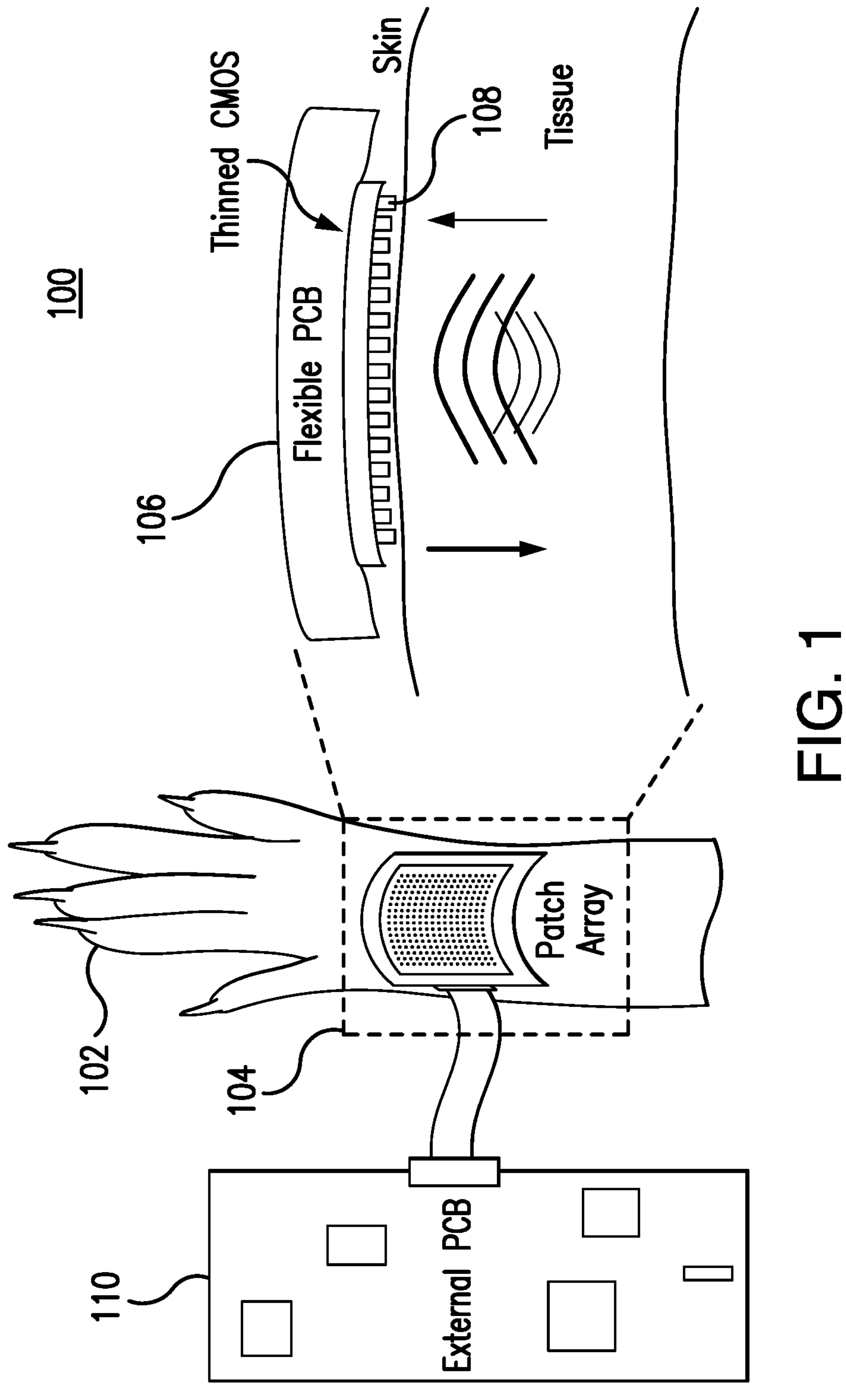
FIG. 1 illustrates a system diagram of the ultrasound phased array patch on flexible CMOS in accordance with some embodiments of the disclosed subject matter.

Throughout the drawings, the same reference numerals and characters, unless otherwise stated, are used to denote like features, elements, components or portions of the illustrated embodiments. Moreover, while the disclosed subject matter will now be described in detail with reference to the Figs., it is done so in connection with the illustrative embodiments.

DETAILED DESCRIPTION

A non-invasive ultrasound phased array patch on flexible CMOS and methods of fabricating thereof are presented. In an exemplary embodiment, a monolithic CMOS phased array is provided that includes one or more ultrasound transducers such that the phased array is capable of operating in multiple modes. For example, in some embodiments, the phased array can provide an imaging mode and a stimulation mode, thus providing high spatial resolution and depth to a target area.

The different operation modes can directly impact the nerves by altering e.g., modulating nerve activity which can be responsible for regulating the function of a population of neurons in both the Central Nervous System (CNS) and Peripheral Nervous System (PNS), to manage and/or cure neurological disorders. In addition, neuromodulation technology can be adapted for delivery of electrical or pharmaceutical agents directly to one or more target areas. As a result, the effectiveness and precision of neuromodulation can depend, at least, on the ability to provide high spatial resolution and depth without causing damage to surrounding tissue.

In some embodiments, while in the imaging mode the phased array uses B-mode ultrasound imaging by employing pulsed ultrasound transmission that produces 2D and/or 3D imaging of a region of interest. Further, in some embodiments, the phased array operates in a stimulation mode by employing a focused ultrasound wave to a selected target area (e.g., target tissue) or it can combine the different operation modes in any suitable manner. In some embodiments, the target area can include focal spot coordinates that are manually selected by an operator using information gathered by the phased array during its operation in imaging mode. In some embodiments, the target area is automatically selected using image processing techniques applied on the images gathered during operation in imaging mode. In some embodiments, imaging and stimulation can be used in an interleaved manner to monitor one or more target areas during stimulation.

Referring to FIG. 1, a system 100 including the CMOS ultrasound phased array integrated circuit (IC) 104 operating in the region of interest is shown. In some embodiments, the CMOS ultrasound phased array IC 104 is designed to have dimensions of approximately 5 mm×5 mm of surface area and 20 μm of thickness. Specifically, the surface area can be fabricated to be small enough for the IC to be placed on the leg of mice 102 for peripheral nervous stimulation, while the thickness makes the IC flexible to conform to the curvature of the body part of interest. Specifically, a CMOS chip can have a thickness of approximately 300-500 μm which corresponds to a CMOS chip that is rigid and lacks flexibility. As a CMOS chip's thickness is reduced using various techniques such as mechanical grinding, etching etc., the CMOS chip can become increasingly flexible. In some embodiments, when interfaced with the piezoelectric transducers, flexibility will depend on the transducer material. Further, the thinned CMOS chip will alleviate any acoustic loading on the transducers, when comparing to rigid CMOS chips.

In some embodiments, a flexible, monolithic CMOS phased array patch IC 104 includes at least two components. The first component includes an ultra-thin integrated circuit (IC) chip 106 that interfaces with one or more ultrasound transducers and the second component includes one or more ultrasound transducers 108 that are integrated on the CMOS phased array patch IC 104. In some embodiments, one or more ultrasound transducers 108 are formed as piezoelectric transducers and convert the electrical energy to mechanical energy when the phased array is operating in stimulation mode. In some embodiments, ultrasound transducers 108 perform the reciprocal conversion when the phased array is operating in imaging mode. In some embodiments, IC chips can be designed in conventional CMOS technology and fabricated in a commercial foundry.

In addition, in some embodiments, the piezoelectric materials for ultrasound transducers 108 include polyvinylidene difluoride (PVDF), zirconate titanate (PZT) or any other suitable piezoelectric material fabricated directly on top of a CMOS chip. In some embodiments, PZT can be used to provide a higher electromechanical coupling coefficient than PVDF, but has higher acoustic impedance mismatch with soft tissue, leading to reflections.

In some embodiments, for small animal model as shown in FIG. 1, system 100 is designed to work at a frequency of 10-15 MHz, and to have a surface area of 5 mm by 5 mm. In some embodiments, lower frequencies and higher surface areas are also possible depending on the different models and design requirements. For example, in some embodiments, ultrasound frequencies for certain diagnostic purposes (e.g., imaging of abdominal area, liver, etc.) can be at a range of 3-10 MHz. In addition, in some embodiments the number of ultrasound transducers 108 can be as high as 1024, leading to a depth of penetration for the focused ultrasound of approximately 10 mm that can be extended to larger penetration depths. In such cases, system 100 can achieve pressures between 0.5 and 10 MPa, which are in line with neural activation pressure requirements, but larger penetration depths can also be achieved depending on the requirements of the region of interest. In some embodiments, the thickness of the IC chip can be reduced to less than 20 μm through various wafer/chip-thinning techniques, resulting in minimized loading effect of the IC chip on the piezoelectricity of the piezoelectric transducer.

System 100 also includes an external printed circuit board (PCB) 110 that controls and configures the CMOS chip for operating in different modes. In some embodiments PCB 110 can be a microcontroller, hardware processor or any other suitable processing machine for configuring the ultrasound phased array 104. In some embodiments, PCB 110 is used for configuring the operation of the phased array 104 in both B-mode imaging and for stimulation mode. In some embodiments, CMOS ultrasound phased array IC 104 can include a low-power wireless transceiver (e.g., bluetooth) to enable communication with a server (not shown) in order to further process the received ultrasound waves.

For example, in B-mode imaging operation mode, PCB 110 controls several parameters of the CMOS ultrasound phased array IC 104 such that pulsed ultrasound waves are steered with a given angle range to cover the region of interest. In some embodiments, one or more parameters of the CMOS ultrasound phased array IC 104 can be controlled and configured by PCB 110. Further, in B-imaging operation mode, the boundaries between different tissue types (muscle, fat, nerve, blood, etc.) generate reflections that are echoed back to ultrasound transducers 108, which convert them into voltages to allow for the image reconstruction. In some embodiments, when PCB 110 configures the CMOS ultrasound phased array IC 104 for stimulation operation mode, then one or more stimulation targets are selected either manually (e.g., by an operator) or automatically and the phase of each ultrasound transducer's excitation voltage is configured to allow focusing on the selected focal region.

As discussed above, in some embodiments, the ultrasound transducers 108 utilize 10-15 MHz ultrasound frequency to provide the best tradeoff between spatial resolution and penetration depth. For example, in some embodiments, given the dimensions of the phased array 104 and the wavelength, the focus dimensions can be approximately 100 μm by 100 μm by 300 μm. In addition, the shorter wavelength also allows the reduction of the thickness of the piezoelectric transducers 108 and thus, the increase of the flexibility of the phased array 104.

FIGS. 2-3 show a fabrication process for the flexible CMOS phased array chip 104. In some embodiments, the fabrication process includes three main components: (1) ultra-thin chip fabrication; (2) integration of the individual ultra-thin CMOS chip with one or more ultrasound transducers of the same size or any suitable size and (3) chip release.

Figures 2A, 2B, 2C:
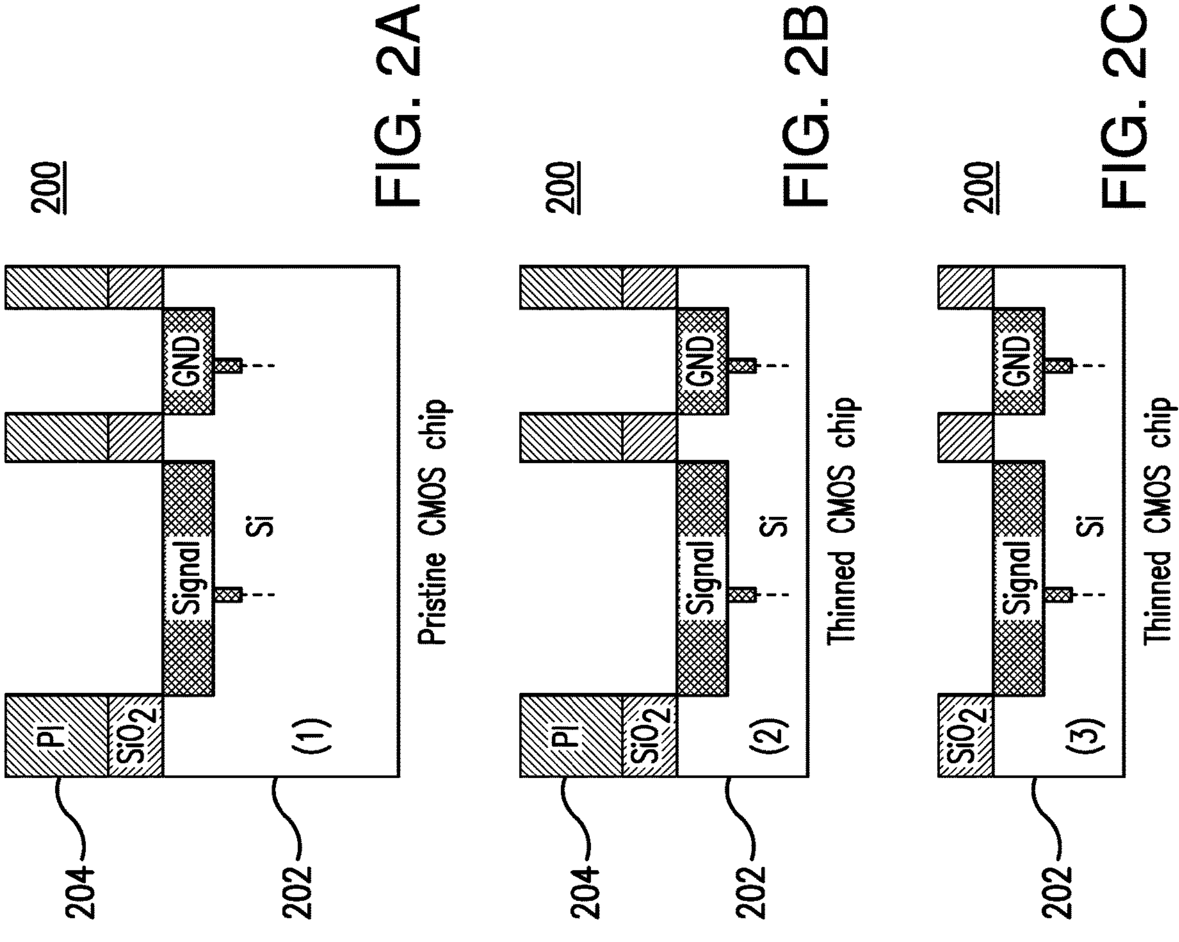
FIGS. 2A-2C illustrate a fabrication process for the CMOS integrated circuit in accordance with some embodiments of the disclosed subject matter.

Specifically, FIGS. 2A-2C show the chip-thinning process for the CMOS integrated circuit prior to integrating the ultrasound transducers 108. FIG. 2A illustrates the pristine CMOS integrated circuit chip die 202 including the passivation layer 204. In some embodiments, the technology node used is a 180 nm CMOS process.

The pristine CMOS chip die 202 is subsequently thinned using one or more wafer/chip thinning techniques in order to minimize the mechanical load on ultrasound transducers 108, as shown in FIG. 2B. For example, in some embodiments, such chip thinning techniques include mechanical grinding and/or deep relative-ion etching (DRIE) or any suitable combination thereof, which are capable of rendering the originally brittle semiconductor wafer (e.g., pristine CMOS) both ultra-thin and flexible. In some embodiments, the chip-thinning process is able to reduce the thickness of a typical CMOS chip die from 500 μm to 20 μm. Such reduction in thickness allows for the CMOS chip die to become flexible and conform to the curvature of the area of interest.

In addition, once the ultra-thin CMOS chip is prepared it is subsequently planarized by uniformly etching the passivation layer 204 using, for example, reactive-ion etching (RIE) or any other suitable etching technique as shown in FIG. 2C. In some embodiments, the ultra-thin CMOS integrated circuit chip can be transferred onto either a rigid or a flexible carrier substrate using a backing material that can be selectively etched away in order to release the chip.

After the CMOS chip is thinned and planarized, as discussed above in reference to FIGS. 2A-2C, the integration and patterning of the ultrasound transducers 108 is performed. In some embodiments, the fabrication process for integrating the ultrasound transducers 108 can include different aspects depending on the type of ultrasound transducer, operation mode, application or any other suitable design parameter. For example, in some embodiments, integrating PZT ultrasound transducers onto the CMOS chip can require multiple fabrication process procedures, as shown in FIGS. 3A-3I.

Figures 3A, 3B, 3C, 3D, 3E:
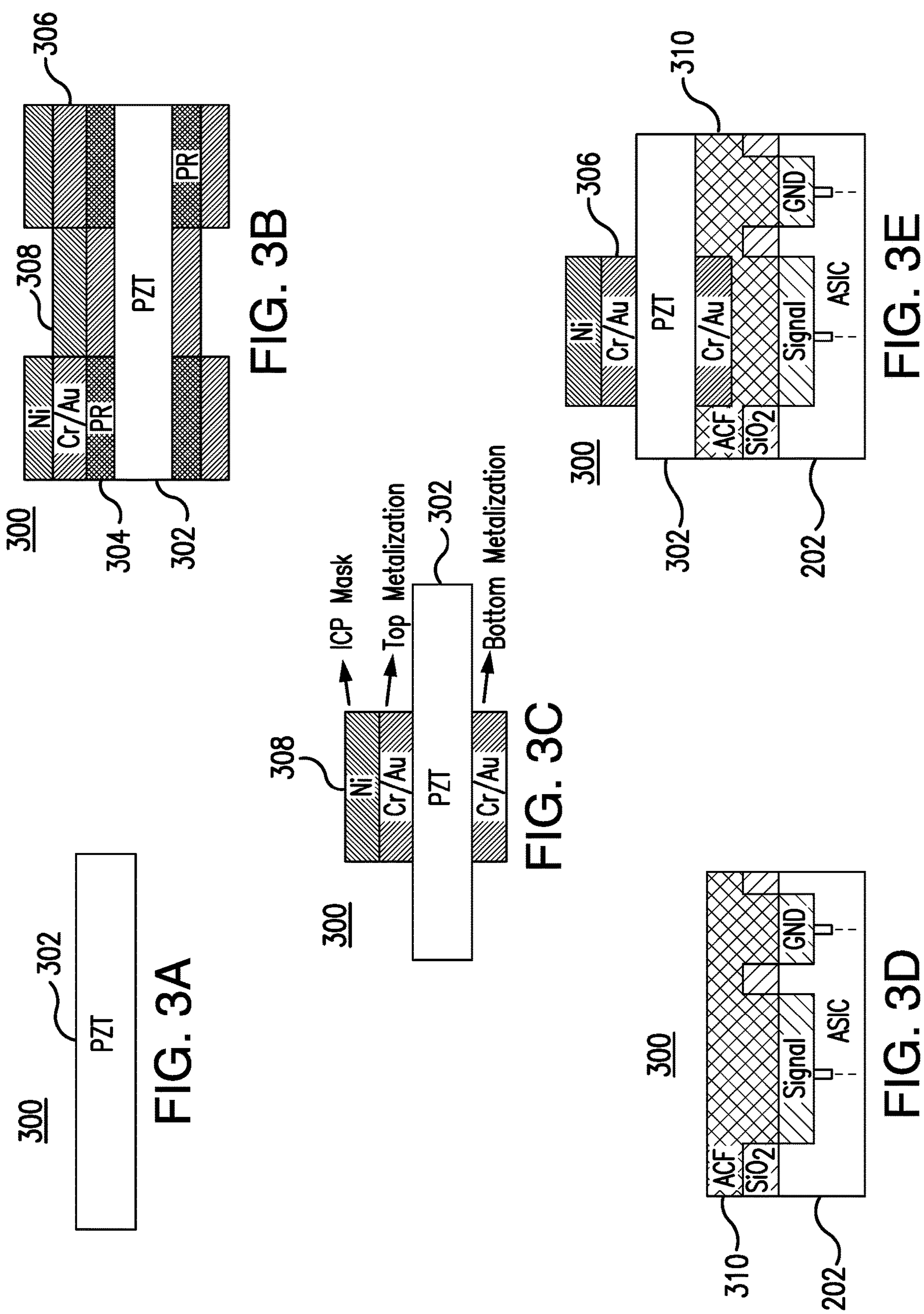
FIGS. 3A-3I illustrate a fabrication process for the CMOS integrated circuit and the ultrasound transducers in accordance with some embodiments of the disclosed subject matter.

Specifically, FIG. 3A illustrates the pristine pre-polled PZT ultrasound transducer chip 302 having a top side and a bottom side prior to the integration onto the ultra-thin CMOS chip. Subsequently, the fabrication process continues with the patterning of a photoresist layer 304 on both sides of the PZT ultrasound transducer chip 302 followed by the deposition of metallic layers 306 and 308 to form a stack on both sides of the PZT ultrasound transducer chip 302. In some embodiments, metallic layers 306 and 308 are formed by materials such as gold, chrome, Nickel or any combination thereof. In some embodiments, the top of PZT ultrasound transducer chip 302 has a chrome/gold and Nickel stack deposited, while the bottom part has a chrome/gold layer.

FIG. 3C, shows the lift-off process that accomplishes the patterning of the deposited metals in order to form a top and bottom metalization. In some embodiments, photoresist layer 304 can be a positive or negative photoresist, thus determining the portions of the chip that become exposed. In some embodiments, any suitable physical vapor deposition technique can be used to form the top and bottom metalization layers. For example, in some embodiments, the top deposited metallic stack of PZT ultrasound transducer chip 302 is formed and patterned using e-beam deposition and electroplating, and the bottom part of PZT ultrasound transducer chip 302 is formed and patterned using e-beam deposition.

Subsequently, the patterned PZT ultrasound transducer chip 302 can be adhered onto the ultra-thin CMOS chip 202. In some embodiments, in order to achieve this, the ultra-thin CMOS chip 202 is coated with a layer of anisotropic conductive film (ACF) 310 or any other suitable adhesive and conductive material, as shown in FIG. 3D. FIG. 3E illustrates the process of adhering the patterned PZT ultrasound transducer chip 302 onto the ultra-thin CMOS chip 202 by applying a mechanical force between the two chips and allowing the adhesive epoxy to cure. In some embodiments, adhesion of the two chips can be accomplished by applying a 150N force and allowing the epoxy to cure at a temperature of 150° C. for approximately 5 sec.

Figures 3F, 3G, 3H, 3I:
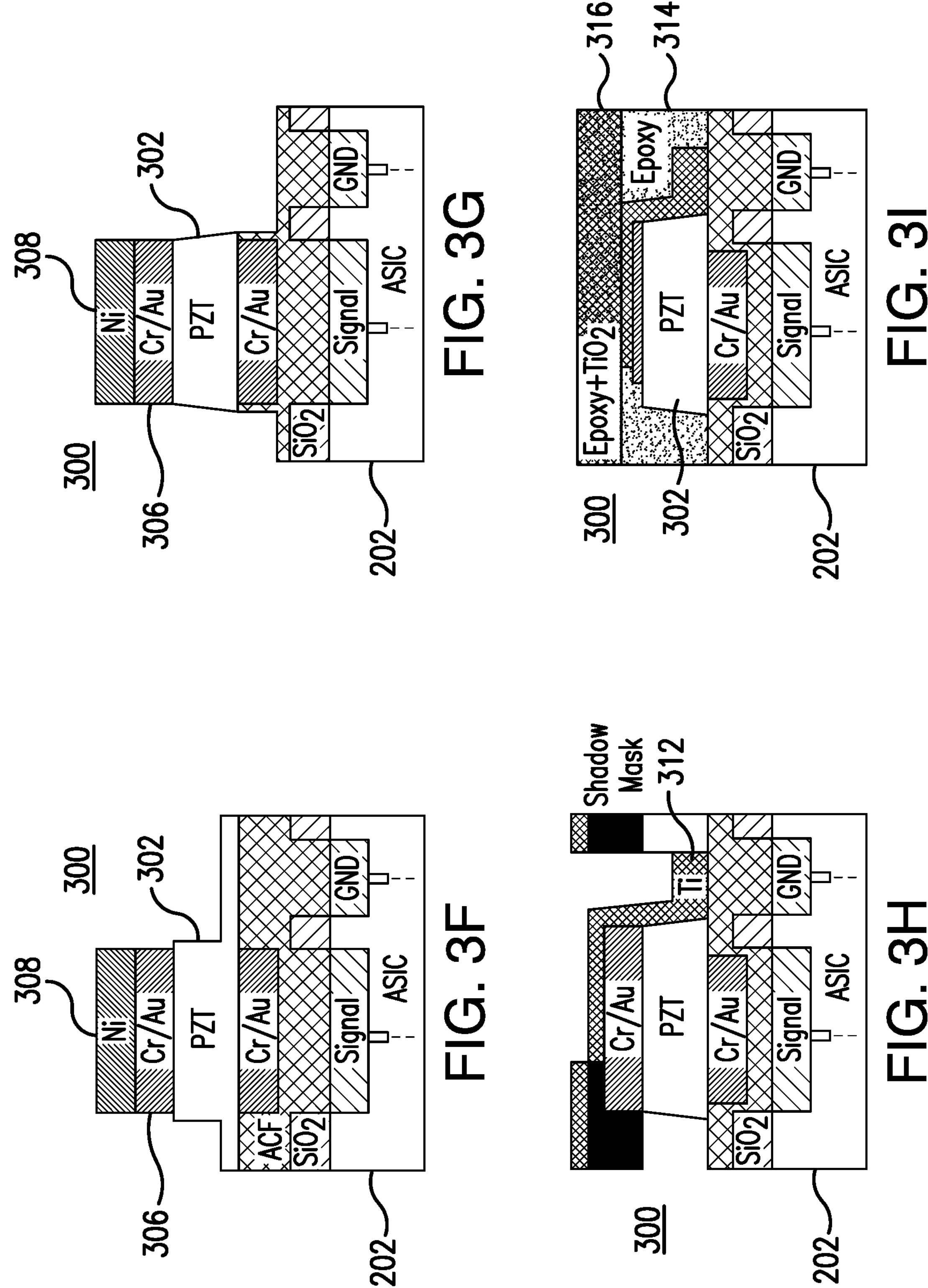

Additionally, the PZT ultrasound transducer chip 302 is further patterned to reduce its thickness as shown in FIGS. 3F-3G. For example, in some embodiments, patterning of 90% of PZT thickness is achieved using a dicing process, whereby a blade of 50 μm is utilized, thus shaping the PZT ultra-thin CMOS chip into PZT pillars 302 with a surface area of 75 μm×75 μm. In some embodiments, PZT pillars can be formed having any suitable design parameters (e.g., dimensions etc.) based on the application and/or region of interest of the CMOS ultrasound phased array patch 104. Further, in some embodiments, the remaining PZT layer and the ACF layer 310 are then etched to further reduce the size and thickness of the chip. In some embodiments, etching includes inductive coupled plasma (ICP) etching, with a Cl and Ar chemistry or any suitable etching technique therein.

FIG. 3H illustrates the subsequent fabrication process of connecting the top of PZT pillars 302 to the CMOS chip contacts. In some embodiments, this is achieved by masking the top of the CMOS chip 202 and PZT pillars 302 using a stainless-steel shadow mask 312 and further performing sputtering using titanium or any other suitable material. FIG. 3I shows the final part of the fabrication process, whereby the kerfs between the PZT pillars 302 are filled with a biocompatible epoxy 314. In some embodiments, an additional Titanium oxide-epoxy composite or any other suitable composite, is deposited on top of the PZT pillars 302 to implement a matching layer 316. In some embodiments, depositing an additional oxide-epoxy composite can be used to configure the transmission coefficients of the phased array to be above 70%.

Moreover, in some embodiments, an alternate fabrication process can be used for any suitable ultrasound transducer. For example, in some embodiments, an anisotropic conductive adhesive is uniformly spin-coated on top of the CMOS chip 202. In some embodiments, such an adhesive conducts vertically, but not laterally in order to avoid shorting adjacent pads. Further, a small piece of commercially available PZT sheet that completely covers the chip is gently placed on top of the adhesion layer to make electrical connection between the input pad of the IC chip and the bottom electrode of the transducer. Subsequently, the etch mask is patterned in order to provide a desired thickness using, for example, micro-powder sandblasting. In some embodiments, etching of the ultrasound transducer chip is followed by forming a metal interconnect between the top electrode of the transducer and the ground pad of the IC chip. In some embodiments, a matching and passivation layers can be added to improve the transmission coupling. In some embodiments, depending on the target tissue, a backing layer for damping of ultrasound waves can be added.

Figure 4:
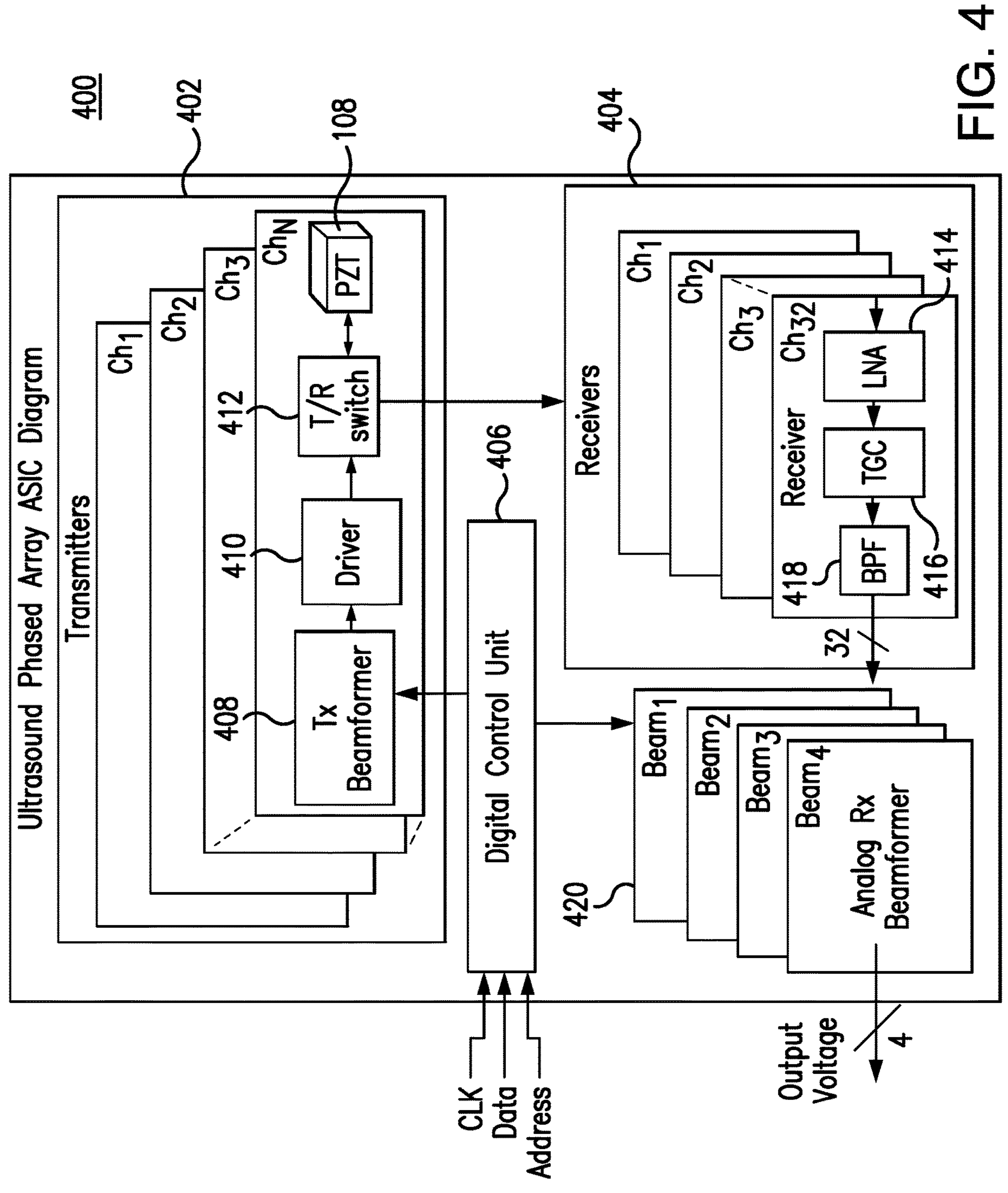
FIG. 4 illustrates a block diagram of the CMOS ultrasound phased array circuit in accordance with some embodiments of the disclosed subject matter.

As discussed above, the CMOS phased array patch IC 104 includes an ultra-thin CMOS chip 202 connected to ultrasound transducers 108. In some embodiments, the CMOS integrated circuit includes three main blocks: a digital control unit 406, a set of receiver channels 404 and a set of transmitter channels 402 as shown in FIG. 4. In some embodiments, the receiver circuits are connected to a subset of ultrasound transducers, while the transmitters are connected to all the transducers in order to maximize focal pressure. Specifically, transmitter channels 402 includes a transmitter beamformer 408 that allows for the focusing of the ultrasound waves, a transmitter driver 410 capable of driving the ultrasound transducers 108 and a transmitter/receiver switch 412. Moreover, receiver channels 404 include a charge amplifier 414, a second stage amplifier 416 and a variable gain amplifier 418 so that the received ultrasound wave (e.g., echo) is compensated in an appropriate manner. The receiver channels 402 are further connected to a set of analog receiver beamformers 420 so as to be electrically coupled (e.g., wired) that perform, among other things, averaging of the received ultrasound waves. In some embodiments, the average power consumption during transmission is proportional to the transmission duty cycle. For example, in some embodiments, for a duty cycle below 10%, the power consumption is below 100 mW. In some embodiments, the technology node used for the system can be a 180 nm complementary metal-oxide-semiconductor (CMOS) process. Finally, the CMOS phased array patch device 104 includes a digital control unit 406 that controls and configures the parameters for the transmitted ultrasound waves.

Moreover, in some embodiments, each of the transmitter channels 402 is divided into two sections. A first section 500 that includes the transmitter beamformers 408 and is responsible for configuring the parameters for the ultrasound transducers and a second section 600 (discussed below in reference to FIG. 6) that includes the transmission driver 410 and is responsible for driving the ultrasound transducers. In some embodiments, each section of the transmitter channel 402 has different power supply domains.

Figure 5:
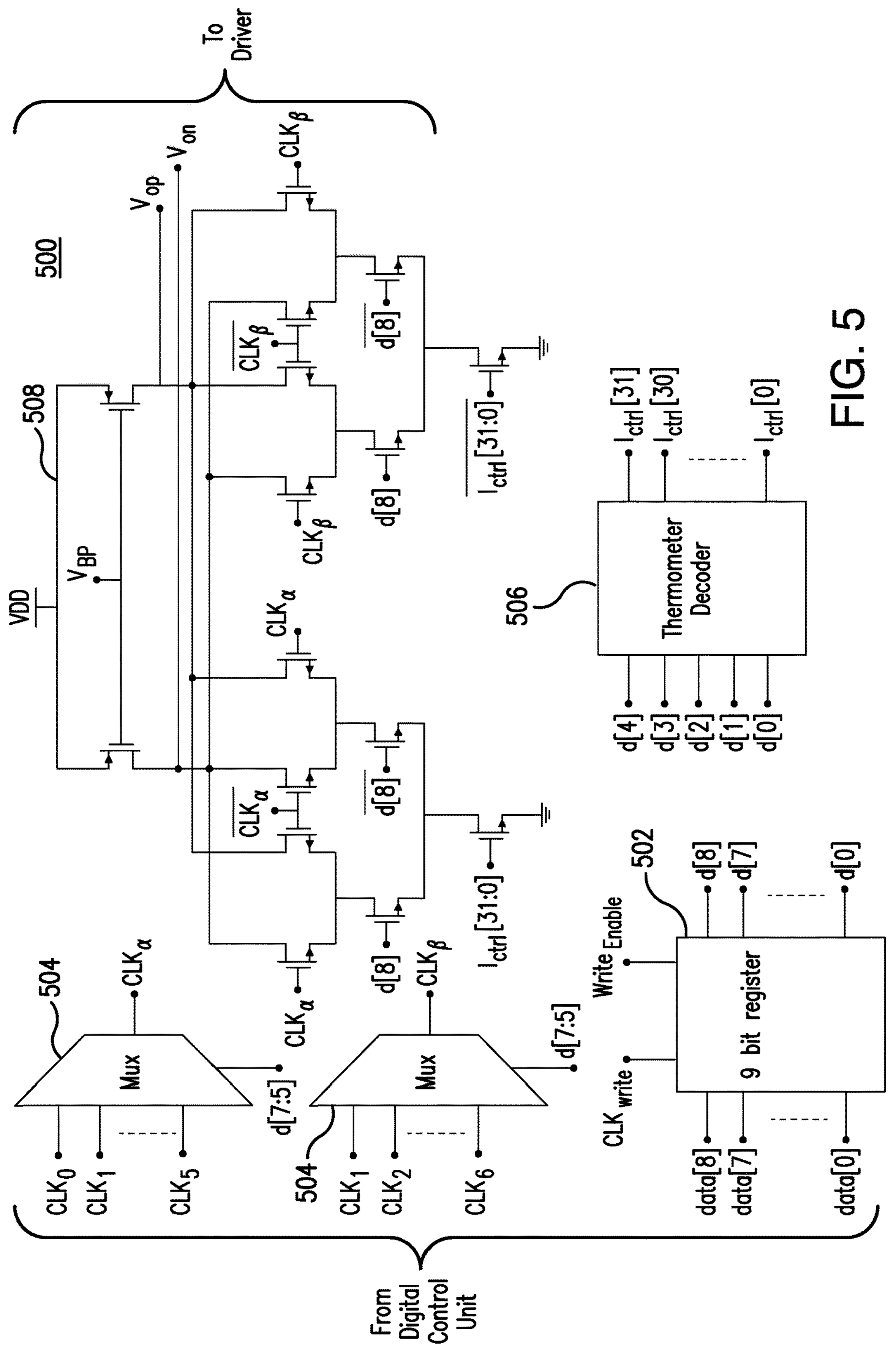
FIG. 5 illustrates a circuit diagram of the transmitter circuit in accordance with some embodiments of the disclosed subject matter.

FIG. 5 shows the circuit of the first section 500, including the transmitter beamformers 408 that receive the input clocks from the digital control unit 406. In some embodiments, the digital control unit 406 outputs 7 clock signals. Transmitter beamformers 408 are responsible for outputting a clock with a specific fine-tuned phase to allow focusing the ultrasound wave in the desired coordinates.

Moreover, first section 500 includes a register 502 with the phase digital information, input multiplexers 504 which perform a coarse selection of the phase, and a thermometer decoder 506 together with a phase interpolator 508, which perform the fine tuning of the clock phase. In some embodiments, register 502 is a 9 bit register. In some embodiments, a pair of multiplexers 504 is used for transmitter beamformers 408. For example, in some embodiments, the input multiplexers 506 select a semi-quadrant of the 180° phase map, by outputting CLKα and CLKβ, where CLKα has an absolute phase difference to the reference clock determined by the outputs bits 7, 6 and 5 of the register 502, and CLKα and CLKβ have a relative phase difference of 30°. The phase interpolator 508 receives CLKα and CLKβ as inputs, and, depending on the 5 least significant output bits of the register, it outputs a clock with a phase interpolated between the phases of CLKα and CLKβ, with a precision of 30° divided by the number of interpolation procedures performed by interpolator 508. In some embodiments, the number of interpolation procedures can be the same as the number of receiver channels. The most significant output bit of the register can add a phase shift of 180° to the output of the phase interpolator, which accomplishes completing the 360° phase map.

Figure 6:
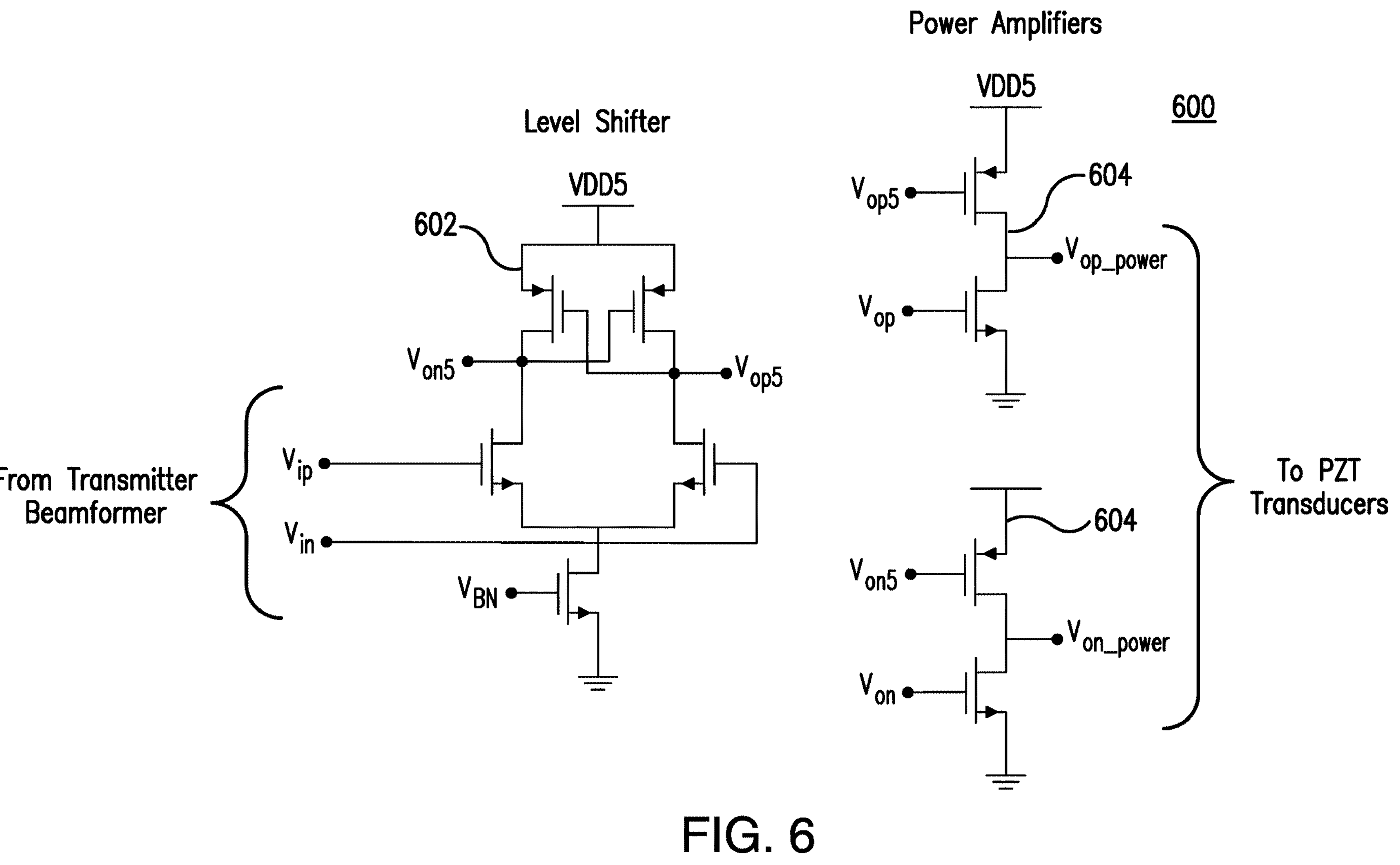
FIG. 6 illustrates a circuit diagram of transmitter driver in accordance with some embodiments of the disclosed subject matter.

FIG. 6 shows the circuit of the second section 600, including the transmitter driver 410. As discussed above, in reference to FIG. 5, the first section 500 of the transmitter outputs a fine-tuned clock signal that allows for the configuration of the ultrasound waves based on a set of parameters. This precise, fine-tuned clock signals is then fed into the transmitter driver 410 that boost the energy controlled clock signal to drive the ultrasound transducers 108. In some embodiments, transmitter driver 410 includes a level shifter 602 and a pair of power amplifiers 604. Specifically, level shifter 602 is responsible for boosting the low voltage power supply to a higher power supply so that it can be subsequently fed into the power amplifiers 604, which are tuned to drive the ultrasound transducers. In some embodiments, level shifter 602 boost a voltage of 1.8 Volt to a voltage of 5 Volts. In some embodiments, two power amplifiers 604 are used instead of one in order to drive the ultrasound transducer 108 with a differential signal, and thus achieve doubling the power sent to the ultrasound transducer 108.

Figure 7:
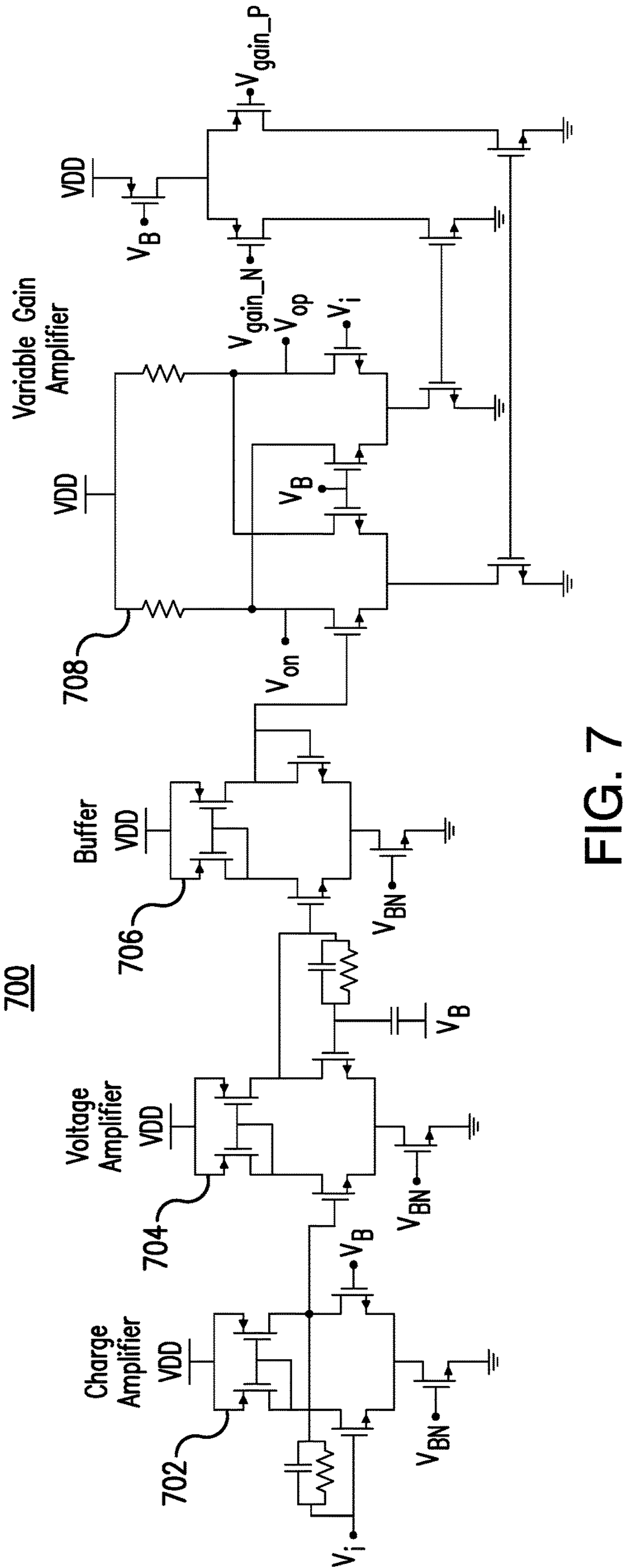
FIG. 7 illustrates a circuit diagram of the receiver low noise amplifier and variable gain amplifier chain in accordance with some embodiments of the disclosed subject matter.

Referring back to FIG. 4, the CMOS ultrasound phased array patch IC 104 includes a receiving section for receiving ultrasound waves (e.g., echoes reflected from the region of interest). In some embodiments, receiver channels 404 include an analog front-end 700, as shown in FIG. 7, and receiver beamformers 420, as discussed above in reference to FIG. 4. The analog front-end 700, includes a low noise charge amplifier 702, a second stage voltage amplifier 704, a buffer 706 and a variable gain amplifier 708, to be able to perform time-gain compensation during signal acquisition.

In some embodiments, the charge amplifier 702 is capable of relaxing the loading effect of the first stage amplification stage on the ultrasound transducer, thus avoiding signal attenuation. Specifically, the charge to voltage gain of the charge amplifier 702 is inversely proportional to the feedback capacitor. In some embodiments, the feedback capacitor can be as low as 100 fF. As a result, in order to avoid severe gain variation due to parasitics, the gain can be set as high as 10. In some embodiments, to increase the gain, a second stage voltage amplifier 704 is also provided to further boost the amplitude of the received signal and to relax the noise constraints of the variable gain amplifier 708. In some embodiments, the variable gain amplifier 708 is used to perform time-gain compensation of the decaying amplitudes of incoming ultrasound waves (e.g., echoes) caused by increased tissue absorption with increasing depth of penetration.

In addition, the variable gain amplifier 708 relaxes the dynamic range in an analog-to-digital converter stage. In some embodiments, this is achieved by continuously adjusting the gain of the analog-front-end depending on the amplitudes of the ultrasound echoes received by the ultrasound transducers 108. In some embodiments, the variable gain amplifier 708 is controlled by two differential voltages (Vgain_P and Vgain_N), which in turn control the tail current of the two input differential pairs. For example, in some embodiments, if $\Delta$Vgain is 0, the output of the VGA is nulled, which can be used if the user wants to completely neglect the ultrasound transducer/skin interface echoes. In addition, in some embodiments, if the $|\Delta$Vgain$|$ is increased up to a saturation value, the gain of the VGA is scaled up.

Figure 8:
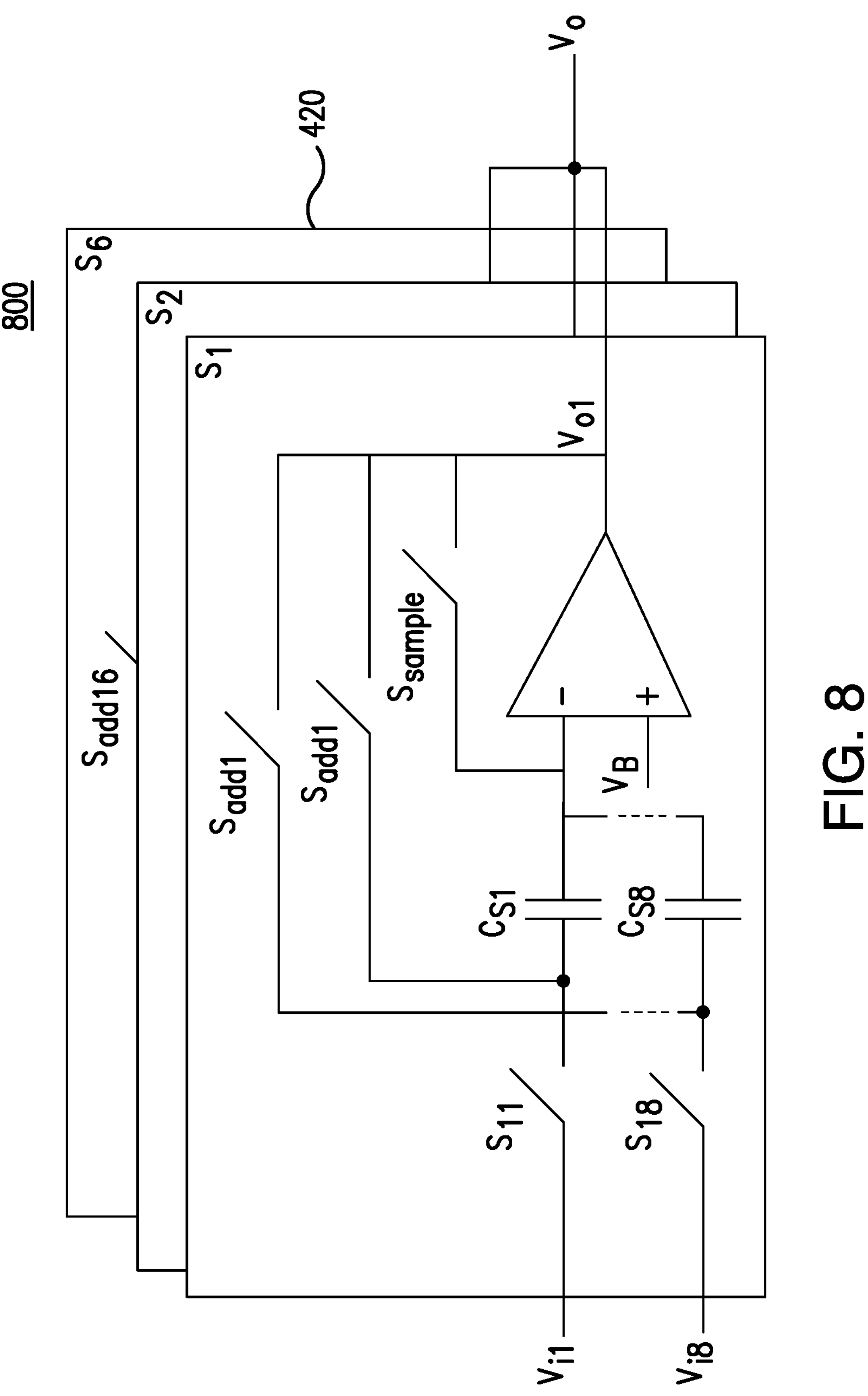
FIG. 8 illustrates a circuit diagram for receiver analog beamformer in accordance with some embodiments of the disclosed subject matter.

Furthermore, after signal amplification in each of the receiver channels, an analog receiver beamformer 420 is used to perform an average between a pre-determined number of channels. For example, in some embodiments, an average between each 8 channels is obtained among the 32 total receiver channels, as shown in FIG. 8.

Specifically, when an ultrasound wave travels the boundary between two tissue types with different acoustic impedances, an ultrasound reflected echo travels back to the ultrasound transducers 108, hitting each transducer at a specific time, depending on their location. As a result, each ultrasound transducer 108 will pick up replicas of the same ultrasound wave, but with different times of arrival, or phases. In some embodiments, the analog beamformer 420, controlled by the digital control unit 406, acquires samples of each echo in order to set all the signals in-phase, and then performs averaging in order to reduce and noise present due to the transmission process. Specifically, given that the ultrasound signals are correlated and the noise is non-correlated, averaging through the analog beamforming 420 leads to an improvement in the signal-to-noise ratio (SNR). In some embodiments, the SNR can be improved by a factor of approximately three (3). The output of the analog beamforming is then buffered and can be sent off-chip, for analog to digital conversion and B-mode imaging.

Figure 9:
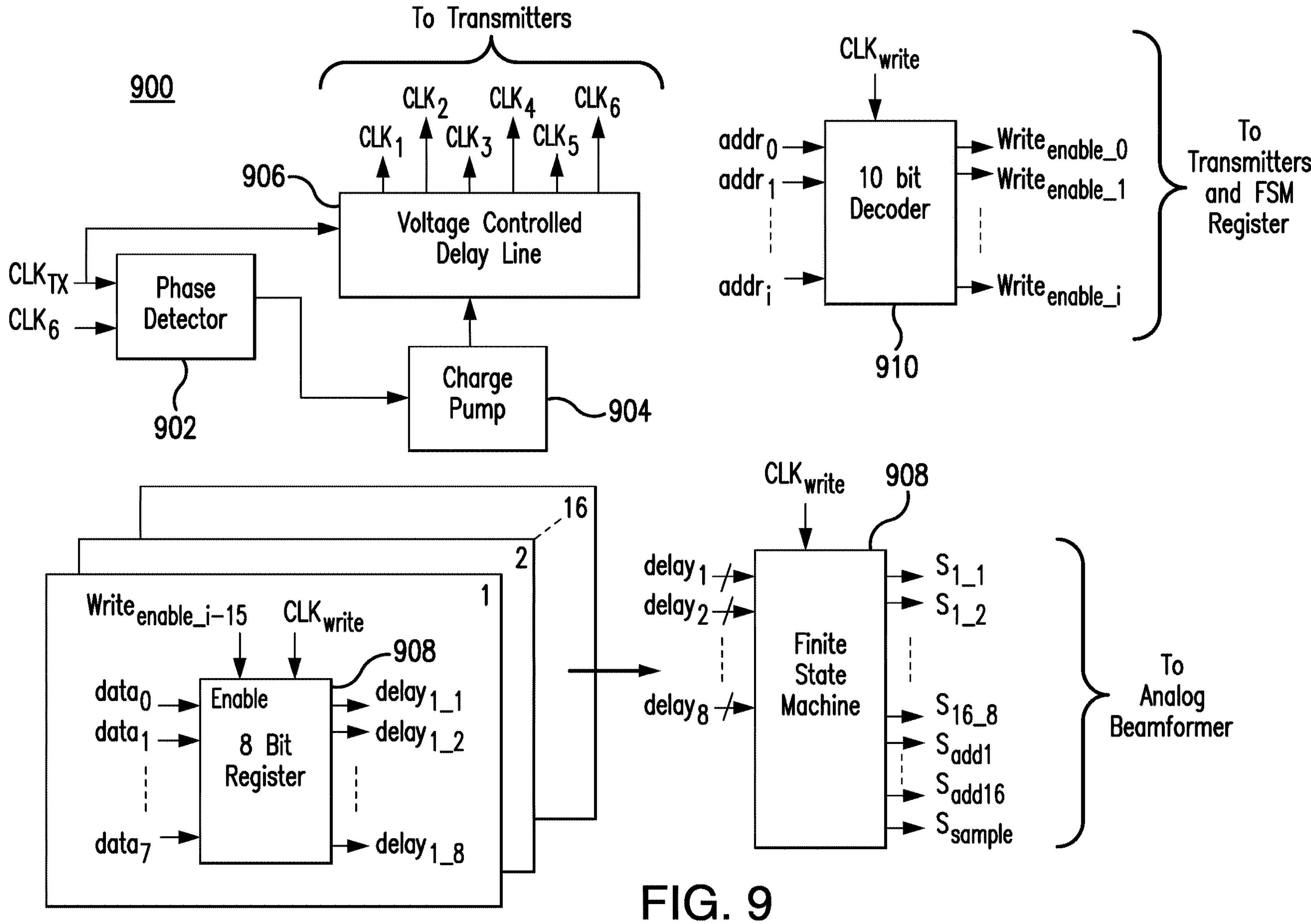
FIG. 9 illustrates a circuit diagram for the digital control unit in accordance with some embodiments of the disclosed subject matter.

FIG. 9 illustrates the digital control unit circuit 406 that configures and controls the parameters for the transmitters 402 and ultrasound transducers 108. Specifically, the digital control unit 406 configures the transmitter's internal registers with the desired phase for stimulation using a phase detector 902, a charge pump 904 and a voltage control delay line 906. In addition, the digital control unit uses a register 908 that operates as a finite state machine for generation of the control signals that are used for beamforming in the receiver paths. In some embodiments, these signals are used to improve the signal to noise ratio (SNR). Further, in some embodiments, the digital control unit circuit 406 performs a delay locked loop using converter 910 to convert an input clock reference into different clocks. In some embodiment the digital control unit 406 generates 7 different clocks with phase shifts of 30°, from 0 to 180°, which are fed into the transmitter channels.

Figure 10:
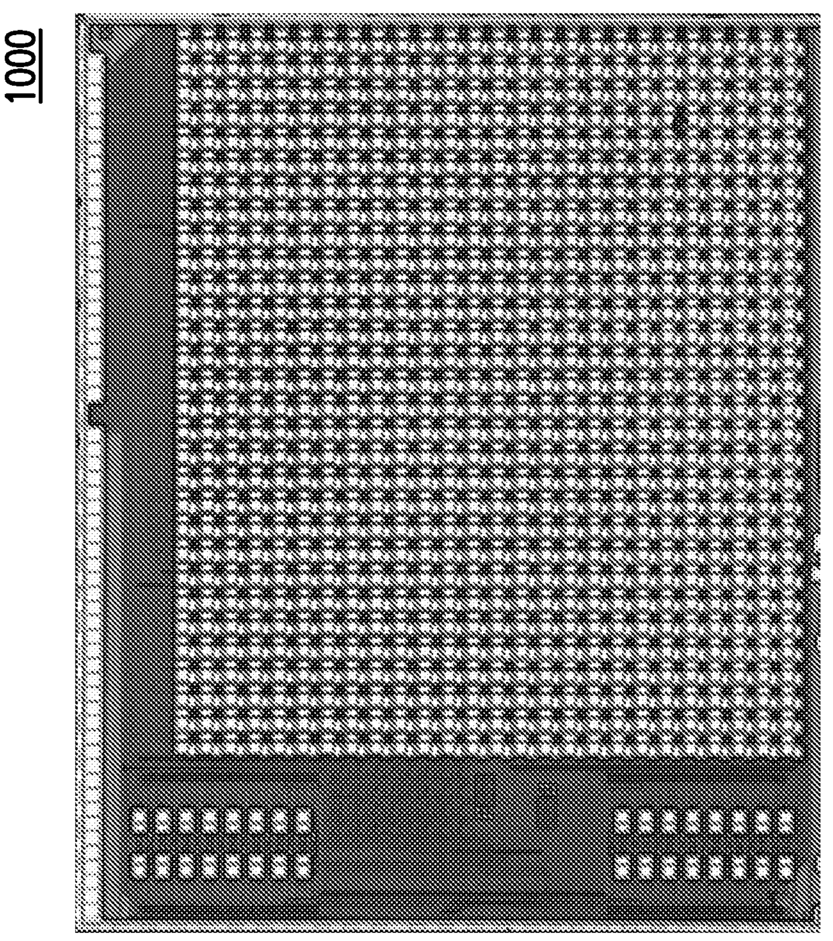
FIG. 10 illustrates a die microphotograph of the phased array CMOS integrated circuit in accordance with some embodiments of the disclosed subject matter.

FIG. 10 shows a microphotograph of a prototype of the CMOS ultrasound phased array patch IC 104. In an exemplary embodiment shown in FIG. 10, the CMOS ultrasound phased array patch 104 includes 676 transmitters and 32 receivers with an overall area of 5 mm×5 mm.

Figure 11:
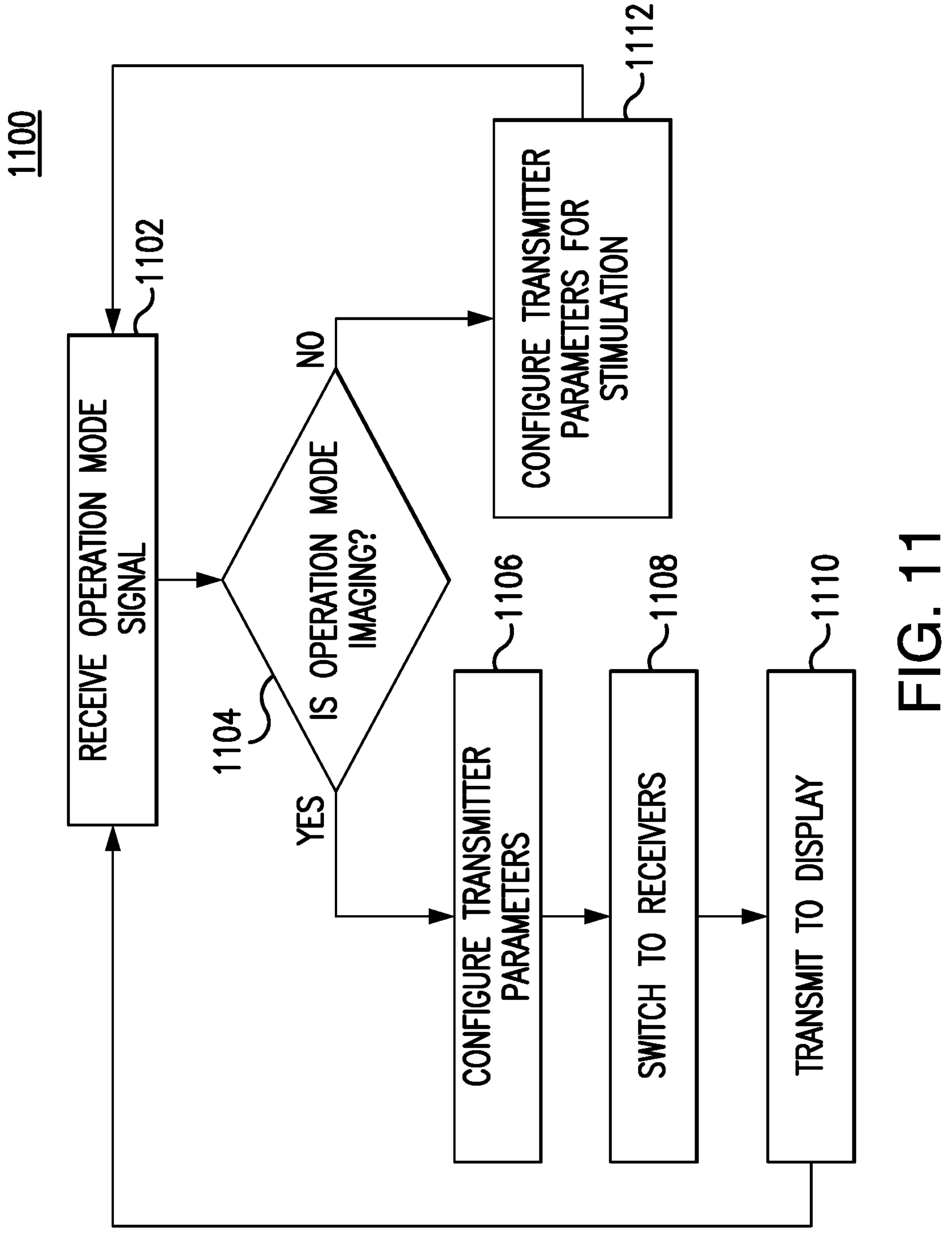
FIG. 11 illustrates a chart of a process of neural monitoring and stimulating using the phased array CMOS integrated circuit in accordance with some embodiments of the disclosed subject matter.

FIG. 11 shows a flow chart of a process when utilizing the CMOS ultrasound phased array patch IC 104. Specifically, at 1102, digital control unit 406 of the CMOS ultrasound phased array patch IC 104 receives one or more signals indicating an operation mode. In some embodiments, the operation mode signals can be transmitted by PCB 110, a server, microcontroller etc. In some embodiments, an operator can manually provide an operation mode signal for the CMOS ultrasound phased array patch IC 104. Subsequently, at 1104, the digital control unit 406 determines the type of operation mode signal. Specifically, if the digital control unit 406 determines that the operation mode signal is that of stimulation (e.g., "NO" at 1104) then the parameters of the transmitter beamformer 408, driver 410 and switch 412 are configured in stimulation mode so as to ensure that the PZT ultrasound transducers 108 are focused and penetrate the target area based on the desired requirements.

If, however, the digital control unit 406 determines that the operation mode signal is that of imaging (e.g., "YES" at 1104) then the parameters of the transmitter beamformer 408, driver 410 and switch 412 are configured in imaging mode so as to ensure that the PZT ultrasound transducers 108 are transmitting to the region of interest. Subsequently, at 1108, the switch 412 performs a switch to the receivers 404 of the CMOS ultrasound phased array IC 104 so that they are configured to receive the ultrasound waves (e.g., echoes) from the region of interest. In addition, at 1110 the reflected ultrasound wave can be transmitted through, for example PCB 110 or any other suitable mechanism, to a display (e.g., VGA etc.) for imaging. Subsequently, the CMOS ultrasound phased array patch IC 104 can set in idle mode and await further operation mode signals. In some embodiments, the displayed image can be further processed using, for example, image processing techniques and a decision to automatically proceed into stimulation mode can be transmitted back to the CMOS ultrasound phased array patch IC 104 allowing for a switch in the operation mode (e.g., from imaging to stimulation.)

The description herein merely illustrates the principles of the disclosed subject matter. Various modifications and alterations to the described embodiments will be apparent to those skilled in the art in view of the teachings herein. It will thus be appreciated that those skilled in the art will be able to devise numerous techniques which, although not explicitly described herein, embody the principles of the disclosed subject matter and are thus within its spirit and scope.

The invention claimed is:

1. A method for fabricating a non-invasive, wearable device for neural monitoring and stimulation, comprising:

thinning a complementary-oxide-semiconductor (CMOS) integrated circuit to a pre-determined thickness thereby causing the CMOS integrated circuit to become flexible;

integrating a plurality of ultrasound transducers onto the CMOS integrated circuit, wherein each of the plurality of the ultrasound transducers includes a top side and a bottom side; and depositing a metal layer on the top side and the bottom side of each of the plurality of ultrasound transducers to form electrodes that are electrically coupled to the CMOS integrated circuit.

2. The method of claim 1, wherein the thinning comprises performing one or more chemical etching procedures.

3. The method of claim 1, further comprising planarizing the CMOS integrated circuit by uniformly etching a passivation layer of the CMOS integrated circuit.

4. The method of claim 3, wherein the uniformly etching of the passivation layer is performed by reactive-ion etching.

5. The method of claim 1, wherein the depositing the metal layer further comprises depositing a photoresist layer on the top side and the bottom side of each of the plurality of ultrasound transducers.

6. The method of claim 1, further comprising patterning the plurality of ultrasound transducers onto the CMOS integrated circuit using a dicing process to form a plurality of ultrasound transducer pillars.

7. The method of claim 6, further comprising filling kerfs formed between the plurality of ultrasound transducer pillars with a biocompatible epoxy.

8. The method of claim 1, wherein the pre-determined thickness is less than 20 um.

* * * * *